United States Patent
Dolce et al.

(10) Patent No.: US 10,398,618 B2
(45) Date of Patent: Sep. 3, 2019

(54) BODY HARNESS

(71) Applicant: Gorbel, Inc., Fishers, NY (US)

(72) Inventors: Betty Dolce, Rochester, NY (US); Brian G. Peets, Fairport, NY (US); Alexander Z. Chernyak, Pittsford, NY (US); James G. Stockmaster, Sodus, NY (US); Benjamin M. Zombek, Pittsford, NY (US); Benjamin Swiatek, Amherst, NY (US); Koby Trout, Williamsville, NY (US)

(73) Assignee: Gorbel, Inc., Fishers, NY (US)

( * ) Notice: Subject to any disclaimer, the term of this patent is extended or adjusted under 35 U.S.C. 154(b) by 78 days.

(21) Appl. No.: 15/187,089

(22) Filed: Jun. 20, 2016

(65) Prior Publication Data

US 2016/0367429 A1 Dec. 22, 2016

Related U.S. Application Data (63) Continuation-in-part of application No. 15/014,679, filed on Feb. 3, 2016.
(Continued)

(51) Int. Cl.
*A61H 3/00* (2006.01)
*G16H 40/63* (2018.01)
*G16H 20/30* (2018.01)

(52) U.S. Cl.
CPC ....... *A61H 3/008* (2013.01); *A61H 2003/007* (2013.01); *A61H 2201/0173* (2013.01); *A61H 2201/0192* (2013.01); *A61H 2201/1215* (2013.01); *A61H 2201/163* (2013.01); *A61H 2201/1621* (2013.01);
(Continued)

(58) Field of Classification Search
CPC ............ A61H 3/008; A61H 2201/1621; A61H 2201/1652; A61H 2201/0192; A61H 2201/163; A61H 2201/5035; A61H 2201/1215; A61H 2201/5058; A61H 2201/1659; A61H 2201/5061; A61H 2201/5043; A61H 2201/5092; A61H 2201/5097; A61H 2201/0173; A61H 2201/5038; A61H 2201/5007;
(Continued)

(56) References Cited

U.S. PATENT DOCUMENTS

| 1,961,119 A | 5/1934 | Ettinger |
| 2,590,739 A | 3/1952 | Hugo |

(Continued)

FOREIGN PATENT DOCUMENTS

| DE | 102013222371 A1 | 5/2015 |
| DE | 102013222372 | 5/2015 |

(Continued)

OTHER PUBLICATIONS

BESI, Inc., BESI and Universal Securement Vests, Mar. 8, 2010, http://www.besi-inc.com/securements.html.*
(Continued)

*Primary Examiner* — Sundhara M Ganesan
*Assistant Examiner* — Shila Jalalzadeh Abyaneh
(74) *Attorney, Agent, or Firm* — Duane C. Basch; Basch & Nickerson LLP (57) ABSTRACT

A body-weight support harness system is disclosed, including an improved body weight support system and method.

13 Claims, 10 Drawing Sheets

Related U.S. Application Data (60) Provisional application No. 62/182,410, filed on Jun. 19, 2015.

(52) U.S. Cl.
CPC .......... *A61H 2201/1652* (2013.01); *A61H 2201/1659* (2013.01); *A61H 2201/5007* (2013.01); *A61H 2201/5023* (2013.01); *A61H 2201/5035* (2013.01); *A61H 2201/5038* (2013.01); *A61H 2201/5043* (2013.01); *A61H 2201/5058* (2013.01); *A61H 2201/5061* (2013.01); *A61H 2201/5092* (2013.01); *A61H 2201/5097* (2013.01); *G16H 20/30* (2018.01); *G16H 40/63* (2018.01)

(58) Field of Classification Search
CPC ...... A61H 2201/5023; A61H 2003/007; G06F 19/3406; A63B 69/24; A63B 69/26
USPC .............................................. 482/69
See application file for complete search history.

(56) References Cited

U.S. PATENT DOCUMENTS

| | | | |
|---|---|---|---|
| 3,222,029 A | | 12/1965 | Hildemann |
| 3,252,704 A | * | 5/1966 | Wilson ............... A61G 7/1017 2/238 |
| 3,330,154 A | | 7/1967 | Habern et al. |
| 3,654,922 A | | 4/1972 | Outcalt |
| 3,699,809 A | | 10/1972 | Komatsu |
| 4,106,335 A | | 8/1978 | Shatto |
| D269,701 S | | 7/1983 | Miller |
| 4,602,619 A | | 7/1986 | Wolf |
| D285,137 S | | 8/1986 | Svensson |
| 4,607,625 A | | 8/1986 | Schenck |
| 4,776,581 A | | 10/1988 | Shepherdson |
| 4,907,571 A | | 3/1990 | Futakami |
| 4,981,307 A | | 1/1991 | Walsh |
| 5,054,137 A | | 10/1991 | Christensen |
| 5,080,191 A | * | 1/1992 | Sanchez ............... A47D 13/086 182/3 |
| 5,190,507 A | | 3/1993 | Iijima |
| D372,982 S | | 8/1996 | Williams |
| 5,632,723 A | * | 5/1997 | Grim ............... A61F 5/022 602/19 |
| 5,660,445 A | * | 8/1997 | Murray ............... A61F 5/3776 297/466 |
| 5,850,928 A | | 12/1998 | Kahlman et al. |
| 5,893,367 A | | 4/1999 | Dubats et al. |
| 5,898,111 A | | 4/1999 | Blankenship et al. |
| 5,988,315 A | * | 11/1999 | Crane ............... A45F 5/00 182/3 |
| 5,996,823 A | | 12/1999 | Dyson |
| 6,079,578 A | | 6/2000 | Dyson |
| 6,125,792 A | * | 10/2000 | Gee ............... A47D 13/046 119/770 |
| 6,135,928 A | | 10/2000 | Butterfield |
| 6,204,620 B1 | | 3/2001 | McGee et al. |
| 6,269,944 B1 | | 8/2001 | Taylor |
| 6,313,595 B2 | | 11/2001 | Swanson et al. |
| 6,315,138 B1 | | 11/2001 | Dyson |
| 6,367,582 B1 | * | 4/2002 | Derby ............... A62B 35/0018 119/857 |
| 6,378,465 B1 | | 4/2002 | Austin |
| 6,464,208 B1 | | 10/2002 | Smith |
| 6,612,449 B1 | | 9/2003 | Otani et al. |
| 6,668,668 B1 | | 12/2003 | Peshkin |
| 6,738,691 B1 | | 5/2004 | Colgate et al. |
| 6,813,542 B2 | | 11/2004 | Peshkin et al. |
| 6,907,317 B2 | | 6/2005 | Peshkin et al. |
| 6,928,336 B2 | | 8/2005 | Peshkin et al. |
| 6,942,630 B2 | * | 9/2005 | Behan ............... A61F 5/0102 128/875 |
| 7,043,337 B2 | | 5/2006 | Colgate et al. |
| 7,120,508 B2 | | 10/2006 | Peshkin et al. |
| 7,185,774 B2 | | 3/2007 | Colgate et al. |
| 7,298,385 B2 | | 11/2007 | Kazi et al. |
| 7,381,163 B2 | | 6/2008 | Gordon et al. |
| 7,461,753 B1 | | 12/2008 | Gatta et al. |
| 7,526,847 B1 | | 5/2009 | Arthur et al. |
| 7,608,847 B2 | | 10/2009 | Rees |
| 7,756,601 B1 | | 7/2010 | Van Dyke et al. |
| 7,832,711 B2 | | 11/2010 | Miyoshi et al. |
| 7,883,450 B2 | | 2/2011 | Hidler |
| 7,973,299 B2 | | 7/2011 | Rees |
| 8,221,293 B2 | | 7/2012 | Hoffman et al. |
| 8,528,866 B2 | | 9/2013 | Fradet |
| 8,844,904 B2 | | 9/2014 | Bogh-Sorensen |
| D749,226 S | | 2/2016 | Cooper et al. |
| 2001/0027149 A1 | | 10/2001 | Bingham |
| 2002/0066711 A1 | | 6/2002 | Taylor |
| 2002/0100642 A1 | | 8/2002 | Mehrman et al. |
| 2003/0015905 A1 | | 1/2003 | Sappei et al. |
| 2003/0057408 A1 | | 3/2003 | Kazerooni et al. |
| 2003/0153438 A1 | | 8/2003 | Gordon et al. |
| 2005/0192159 A1 | * | 9/2005 | Jackson ............... A45F 3/14 482/23 |
| 2006/0229164 A1 | | 10/2006 | Einav |
| 2007/0004567 A1 | | 1/2007 | Shetty et al. |
| 2007/0256890 A1 | * | 11/2007 | Petzl ............... A62B 35/0018 182/3 |
| 2007/0278036 A1 | | 12/2007 | Barta et al. |
| 2008/0287268 A1 | | 11/2008 | Hidler |
| 2009/0215588 A1 | | 8/2009 | Riener et al. |
| 2010/0137772 A1 | | 6/2010 | Tanaka et al. |
| 2011/0017546 A1 | * | 1/2011 | Nichols, Jr. ........ A62B 35/0018 182/3 |
| 2011/0100249 A1 | | 5/2011 | Ipsen |
| 2012/0000876 A1 | | 1/2012 | Bergenstrale et al. |
| 2012/0018249 A1 | | 1/2012 | Mehr |
| 2012/0283794 A1 | * | 11/2012 | Kaib ............... A61N 1/3968 607/5 |
| 2013/0153334 A1 | | 6/2013 | Crew et al. |
| 2014/0206503 A1 | | 7/2014 | Stockmaster et al. |
| 2014/0276306 A1 | * | 9/2014 | Dreske ............... A61H 3/008 602/19 |
| 2015/0320632 A1 | | 11/2015 | Vallery et al. |

FOREIGN PATENT DOCUMENTS

| | | |
|---|---|---|
| EP | 2402279 | 4/2014 |
| GB | 1207697 | 10/1970 |
| JP | 04202972 | 8/1994 |
| JP | 11004858 | 1/1999 |
| JP | 2005279141 | 3/2004 |
| WO | WO 2014/131446 | 9/2014 |

OTHER PUBLICATIONS

PCT/US2014/012434 an Unofficial Copy of an International Search Report and Written Opinion dated Jun. 18, 2014 for PCT/US2014/012434 filed Jan. 22, 2014, Inventor James G. Stockmaster, et al.
PCT/US2016/016414 an Unofficial Copy of an International Search Report and Written Opinion dated Jun. 2, 2016 for PCT/US2016/016414 filed Feb. 3, 2016, Inventor James G. Stockmaster et al.
U.S. Appl. No. 14/160,613—Co-Pending U.S. Patent Application filed Jan. 22, 2014.
Unofficial copy of Chinese Office Action dated Dec. 12, 2016 for Chinese Application CN201480017417.7.
International Family Information for CN101595055A.
International Family Information for CN102123687A.
PCT/US2016/038353 an unofficial copy of International Search Report and Written Opinion dated Dec. 28, 2016 for PCT/US2016/038353 filed Jun. 20, 2016; Applicant Gorbel Inc.
PCT/US2016/038353 an unofficial copy of an Invitation to Pay Additional Fees and where applicable protest fee dated Sep. 6, 2016; Corresponds to U.S. Appl. No. 15/187,089; Inventor Dolce et al.
EP14742789.2—A European Search Report and Search Opinion dated Jul. 4, 2016.

(56) References Cited

OTHER PUBLICATIONS

KR 10-2015-7022342 an Unofficial Copy of a Korean Office Action (With English Translation) dated Aug. 11, 2016 for Korean Patent Application 10-2015-7022342 Filed Jan. 22, 2014.
Unofficial copy of Japanese Office Action dated Jun. 19, 2018 for Japanese Application 2015-555223 dated Jun. 19, 2018.
An Unofficial Copy and English translation of a Korean Office Action dated Oct. 22, 2018 for Korean Application 10-2017-7024743 dated Oct. 22, 2018.
EP16747213.3—An Unofficial Copy of a European Search Report and Written Opinion Dated Sep. 4, 2018 for European Patent Application EP16747213.3 dated Sep. 4, 2018.

* cited by examiner

BODY HARNESS

This application claims priority from U.S. Provisional Patent Application No. 62/182,410 for a BODY HARNESS, by B. Dolce et al., filed Jun. 19, 2015; this application is a continuation-in-part of co-pending U.S. patent application Ser. No. 15/014,679 for a MEDICAL REHAB BODY WEIGHT SUPPORT SYSTEM AND METHOD WITH HORIZONTAL AND VERTICAL FORCE SENSING AND MOTION CONTROL, by J. Stockmaster et al., filed Feb. 3, 2016, both of which are hereby incorporated by reference in their entirety.

The system disclosed herein relates to an improved body harness used for the support of an individual or patient, for example, a harness used with a body-weight support system, such as the Medical Rehab Body Weight Support System disclosed in co-pending U.S. Patent Application Ser. No. 15/014,679 by J. Stockmaster, et al., filed Feb. 3, 2016, which is hereby incorporated by reference in its entirety, or with fall-arrest and similar body support systems.

BACKGROUND AND SUMMARY

The process of providing rehabilitative services and therapy to individuals with significant walking deficits and other physical impairments presents a challenge to even the most skilled therapists. For example, patients suffering from neurological injuries such as stroke, spinal cord injury, amputees, or traumatic brain injury often exhibit an inability to support themselves, poor endurance or walking patterns that are unstable. Such deficiencies make it difficult, at best, for the patient and therapist to engage in particular exercises, therapies, etc. Accordingly, it is increasingly common for such therapies to involve some sort of body-weight support system to reduce the likelihood of falls or other injuries, while enabling increased intensity or duration of the training or therapy.

Some existing support systems obstruct a therapist's interaction with the patient, by presenting barriers between the patient and the therapist. Furthermore, existing harness systems present problems when they slip or "ride-up" the patient's torso. Some harnesses also present a problem when trying to put them on to patients—particularly patients that may be seated. In light of the current harness systems there is a need for an improved harness system that overcomes the limitations characterized above.

Patient discomfort while wearing a rehabilitation harness can be a barrier for many therapists to use body weight support and fall protection systems. Impingement of harness straps into the groin and axilla can make it difficult for patients to focus on their form, and challenging for therapists to encourage intensity during functional tasks. The need for a second set of hands or additional time to properly place harnesses can result in the loss of valuable therapy treatment minutes. The disclosed body harness embodiments provide a solution that addresses traditional harness 'pain points' and enables patients and similar users to comfortably and safely practice gait, balance and fall management exercises.

Disclosed in embodiments herein is a harness for supporting a person engaged in a weight-bearing therapy, comprising: an adjustable abdominal support around the torso of the person, said support being located generally below the sternum; a pair of straps, said straps extending downward along the front of the person's torso to the abdominal support, said straps combining in the rear and extending along the back of the person's torso to the abdominal support; an adjustable, padded chest strap operatively connected to said straps and/or said abdominal support; and leg support (e.g., separate leg bands or shorts), releasably suspended from said abdominal support.

Also disclosed in embodiments herein is a body harness, comprising: a torso support unit including a padded posterior column, an adjustable abdominal support adapted to be placed around a torso of a user, at a location generally below a user's sternum, said abdominal support including an adjustable waistband operatively connected to said posterior column with padded waistband ends where one waistband end may be placed in overlapping contact with an opposite waistband end for securing using a hook-and-loop fastening system, said waistband further including at least one secondary waistband encompassing at least part of the adjustable waistband for further cinching the adjustable waistband, an adjustable chest band operatively connected to said posterior column above the waistband, said chest band including chest band ends where one chest band end may be placed in overlapping contact with an opposite chest band end for securing using a hook-and-loop fastening system, said chest band further including at least one secondary chest band encompassing at least part of the chest band for further cinching the chest band; at least one leg support, releasably suspended from said torso support unit; and a pair of support straps each operatively coupled at a first end to the torso support unit adjacent the top of the padded posterior column, and each releasably coupled at a second end to the torso support unit a location on each of the respective waistband ends.

The various embodiments described herein are not intended to limit the disclosure to those embodiments described. On the contrary, the intent is to cover all alternatives, modifications, and equivalents as may be included within the spirit and scope of the various embodiments and equivalents set forth. For a general understanding, reference is made to the drawings. In the drawings, like references have been used throughout to designate identical or similar elements. It is also noted that the drawings may not have been drawn to scale and that certain regions may have been purposely drawn disproportionately so that the features and aspects could be properly depicted.

DETAILED DESCRIPTION

Figure 1:
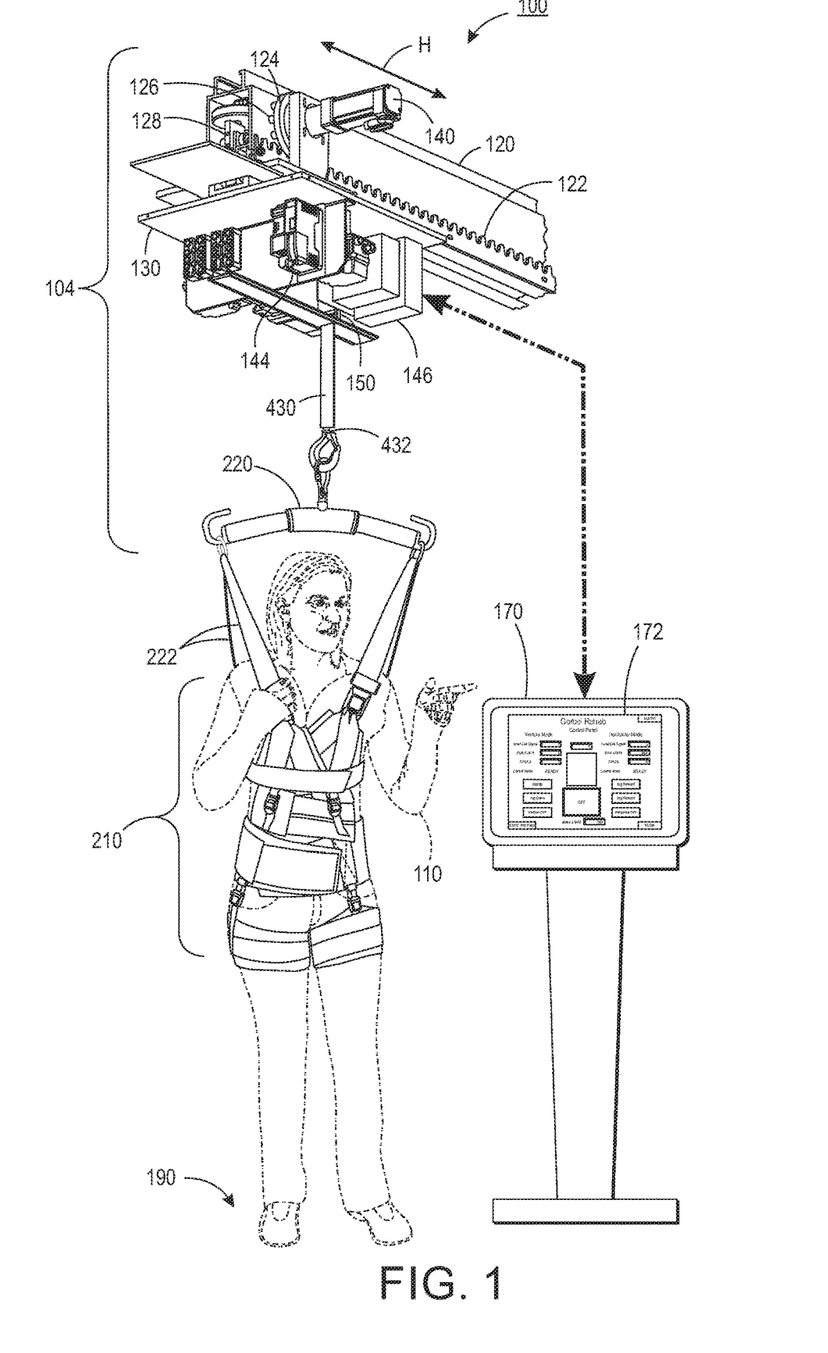
FIG. 1 is an exemplary embodiment for a system supporting a person or user in a harness.

Referring to FIG. 1, depicted therein is a system 100 (e.g., a SafeGait™ 360° Balance and Mobility Trainer system from Gorbel, Inc.) for supporting a selectable portion (e.g., percentage) of the weight of a person or patient 110 using a body harness 210 attached via straps 222 to spreader bar 220 and belt 430. In a general sense, the system comprises a track 120. Although not expressly illustrated in FIG. 1, the depicted embodiments contemplate the use of a spreader bar 220 that provides at least two lockable restraints through which straps 222 are threaded, such that the straps may be locked in a manner whereby more or less support is provided to the person though one strap or one side of a set of straps (e.g., front or back straps). For example, the back straps could be slightly shortened in order to provide more support to the person from the back.

Figure 2:
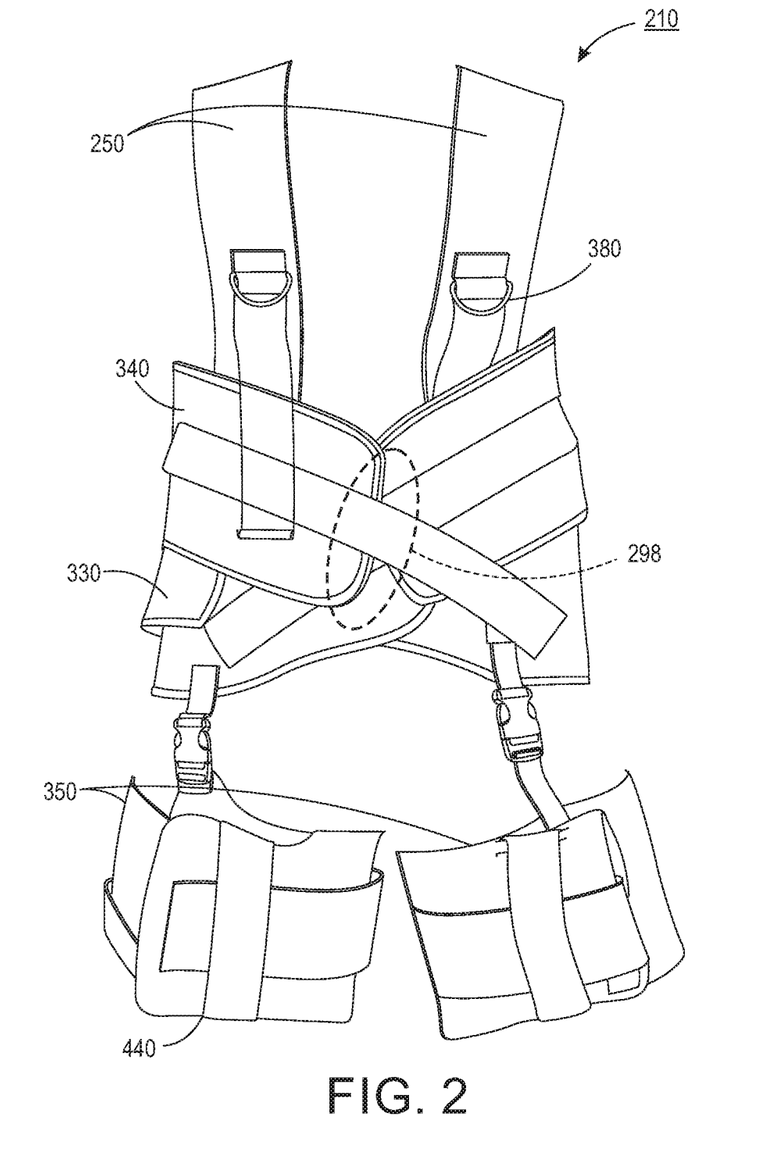
FIGS. 2 and 3 are respective front and rear views of an exemplary harness.
Figure 3:
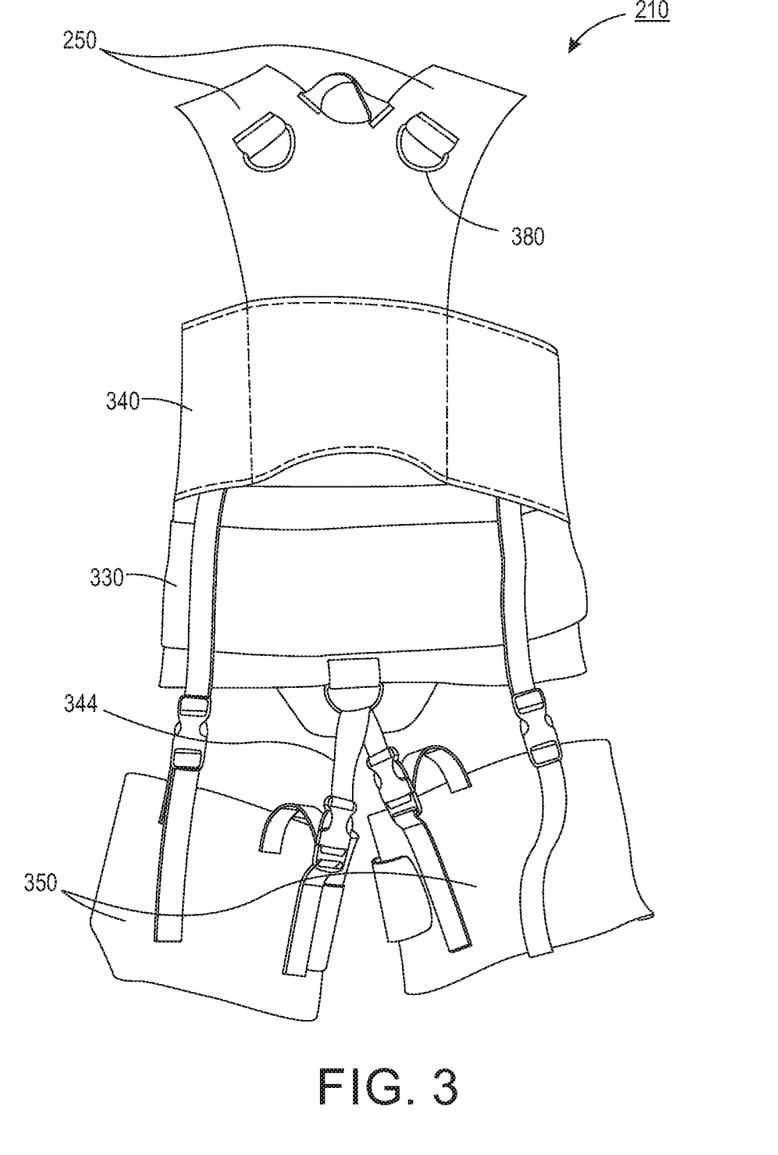

Having described a general embodiment for a system employing a body harness in accordance with the disclosed embodiment, attention is turned to the details of the harness and exemplary embodiments thereof, for example, FIGS. 2-3. In contrast to conventional harnesses, the disclosed embodiments offer an improved application, comfortable materials and unique designs intended to prevent uplifting forces from causing the harness to 'ride up' into sensitive patient areas. As described herein, the torso component or unit of the disclosed body harness features a padded posterior column manufactured with breathable material to provide patients with comfortable, postural support. Each torso component is designed to fit a broad range of body dimensions, and preferably a single harness can accommodate the span of two traditional harness sizes, thereby reducing costs and reducing the complexity of fitting harnesses to users. Furthermore, color coding makes sizing identification easy, and private, in a busy therapy setting. Donning shoulder straps enable a single therapist to position and secure the harness to a patient.

As another example, the waistband is designed with an interior structure that comfortably counters uplifting forces from body-weight support systems to maintain harness position on the patient. The spreader bar straps attach, not to the shoulder straps or a chest piece, but to the padded waistband. This configuration avoids the chest piece from riding up into the axilla and causing discomfort. And, in one embodiment, a 'gripping' material is incorporated into at least the waistband to maintain its position against the patient's clothing.

A padded posterior column is also integrated with a chest band that is attached to the column above the waistband of the torso component. The padded chest band is designed to provide a comfortable, secure fit on the patient. As noted above, the chest band is free from direct connection to an overhead body-weight support system, and thus minimizes such components 'riding up' and causing discomfort. Both the waist and chest bands feature central hook-and-loop attachment bands, as well as secondary 'hug' belts for a comfortable, secure 'embrace.'

The disclosed harness embodiments also include interchangeable leg cuffs with adjustable alignment straps. A modular design allows for interchangeability between leg cuffs, which are placed around a user's (upper) thigh, and in combination with the torso component accommodates patients with various body types. The leg cuffs are removable, with quick-release buckles providing flexibility and enabling 'fitting' combinations. The color-coded leg cuff alignment strap allows therapists to easily match leg cuffs to torso units and to correctly align cuffs on the patient. And, as with the torso component, the leg cuffs each Include at least one secondary 'hug' strap to provide for a snug, secure yet unrestricted 'embrace.' Lastly, as described in more detail herein, the disclosed body harness system may be used with various body-weight support systems as well as fall protection devices.

Although an exemplary strap and harness are depicted, it should be appreciated that various alternative harness configurations and support devices may be employed in accordance with the system, and that the intent is not to limit the scope of the disclosed system to the harness depicted. Alternative harness configurations and details may be employed, where several designs of the harness 210 are contemplated without the spreader bar. Harness 210 may include a backplate or posterior component that is operatively connected, via straps or similar adjustable connections, to a sternum catch pad.

Figure 11:
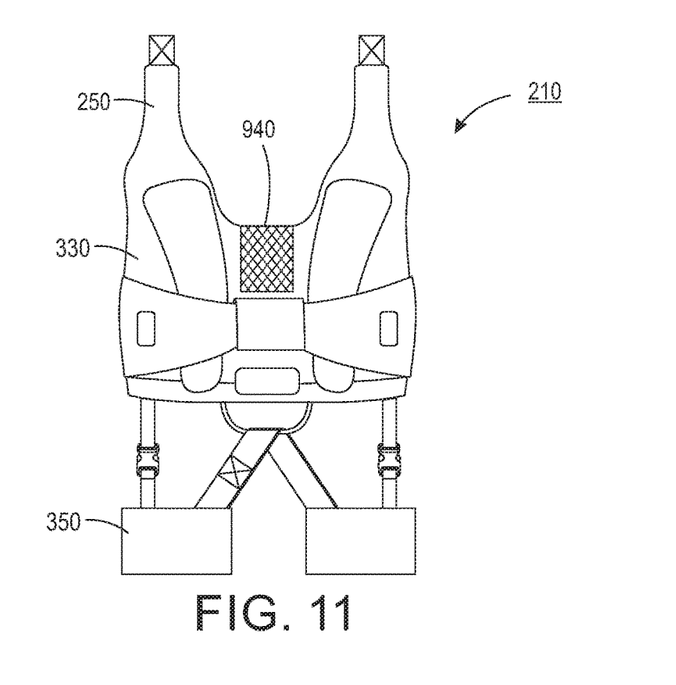

In another alternative such as depicted in the FIG. 11 harness design a sternum catch pad has an opening through which the patient places his/her head, such that the pad is placed across the shoulders, over the head and then down the chest or front of the patient where the sternum catch pad is connected to torso pads that are similarly connected to the back plate and extend or wrap around respective sides of the patient's torso. Also, a pair of thigh pads or cuffs may be provided as illustrated in each of FIGS. 1-4 and 10-14, each one extending or wrapping around one of the patient's thighs (e.g., on or below the patient's quadriceps muscles), and each being adjustably connected to the backplate or posterior unit as well as to a connection on the chest pad and/or optional junction pad. In one configuration the design may include a junction pad, a torso pad, sternum catch pad and thigh pads all connect to or through the junction pad. As will be appreciated, the harness 210 may have various configurations. Furthermore, one or more of the posterior backplate and the pads attached thereto may include supporting structures such as metal rods, molded foam padding layers (possibly including impact hardening foam to disperse load forces), straps and associated adjustments and connectors, along with breathable materials such as meshes and the like.

Depicted in several figures is a body harness 210 for supporting a person 110 engaged in a weight-bearing therapy. In the embodiment of FIGS. 2-3, for example, the harness 210 includes an adjustable abdominal or torso support component 330 around the torso of the person or user, the support being located generally below the sternum of the wearer. Also included are a pair of shoulder adjustment straps 250, the straps extending downward along the front of the person's torso (FIG. 2) to the chest strap 340, and as illustrated in FIG. 3, the straps combine in the rear (posterior) and extend along the back of the person's torso to the abdominal support. An adjustable, padded chest strap 340 is also operatively connected to the shoulder straps and/or to the abdominal support to provide additional contact and support surface between the harness and the wearer. Leg support such as the separate leg bands 350 are releasably suspended using straps and buckles to connect the leg supports to the abdominal support 330 and/or the straps 250. In the embodiment of FIGS. 2-3, the leg support comprises a pair of wide bands (e.g., greater than 3 inches, and preferably 4-7 inches) that wrap around a wearer's upper leg. The inner padded band is overlapped and affixed with a first hook-and-loop fastening strip (e.g., Velcro®) that has mating-material surfaces on the band itself. Next, to assure that the padded band is snugly fit, an outer adjustable band is cinched and attached to itself, again using the hook-and-loop fastener system, or other conventional belt fastening means such as buckles (e.g., hole and prong), slides, overlapping weaves, etc.

As will be appreciated, the use of straps and buckles or similarly separable/releasable members to connect the leg supports to the abdominal support, as well as at other locations, not only allows the adjustment of the position of the leg supports but also contemplates a modular design whereby there may be different component sizes for both the upper harness components (e.g., abdominal support and chest strap), leg straps, and the components may be mixed and matched on an as-needed basis in order to properly fit each person's body size and shape. Such interchangeability allows sizing of the leg supports separately from the balance of the harness.

Figure 4:
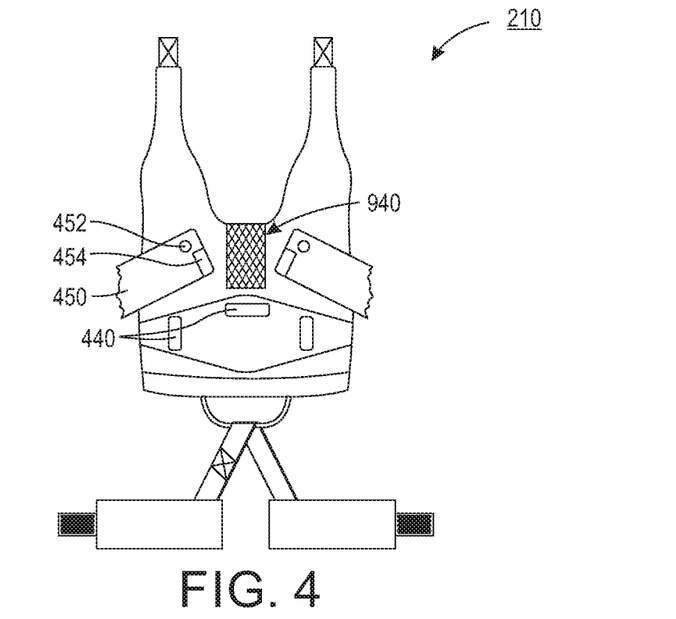
FIGS. 4-11 are illustrative representations of various features and alternatives for the harnesses depicted in FIGS. 1-3.

Also illustrated in FIGS. 2-3 is a chest strap 340 attached in an angled or diagonal manner front-to-back to provide an adjustable position based upon the person's physical size and body shape, and thereby increase the contact area of the harness with the person's torso. Referring also to FIG. 4, for example, the chest strap 450 may be terminated or connected at left and right ends on the back of the harness, and the ends thereof each allowed to independently pivot about a pivot point 452 and then be re-seated with a hook-and-loop fastening (e.g., Velcro®) strip 454, once again allowing the angular position of the chest strap to be further adjusted and controlled. In the alternative embodiments of FIGS. 10 and 11, the abdominal support 330 are presented showing alternative ways in which diagonal members or straps 920 and or a laced or flexible adjustment 940, on the back of the harness, may be employed so as to provide adjustability in the torso fitting to expand the range of body sizes that the harness may be used with. Accordingly, at least one of the harness components may include a self-tightening or self-contracting feature, where the circumference of the component decreases as the length (or height) of the component increases due to an applied force. In such a configuration, for example in a leg support or leg cuff, as more weight is borne by the leg support, the support constricts and contacts the user's leg with greater force as well.

Figure 9:
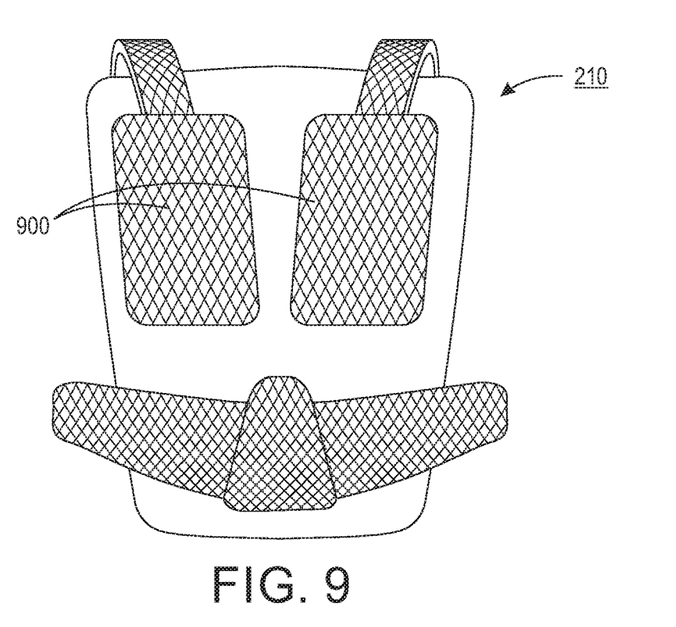
Figure 10:
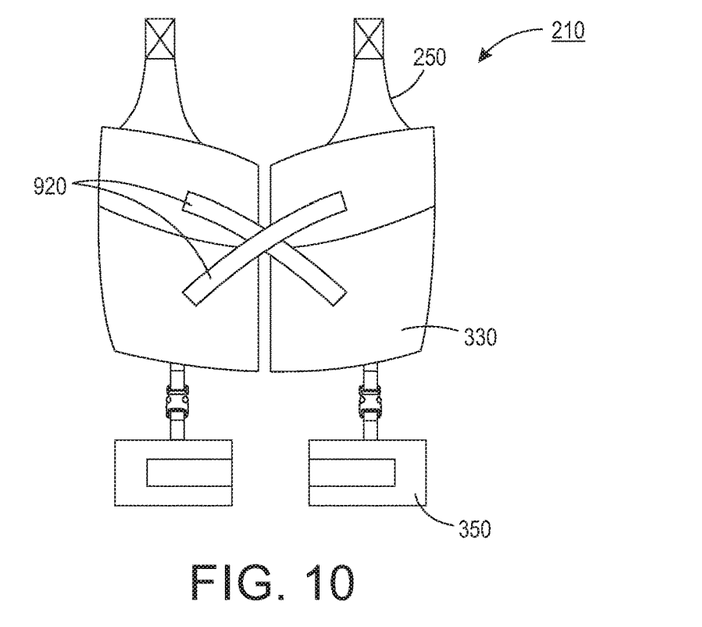

Another feature of the abdominal support and leg supports is the use of a flexible handle (see 440 in FIGS. 2-4) improving the ease of grasping the harness component, even while attached to the person, to assist in positioning of the harness on the person. Such handles are contemplated for use with at least one of the abdominal support, chest strap and leg supports. It will also be appreciated that padding or similar material may be employed at various positions in the harness, where such padding relieves pressure of discomfort by shifting pressure to other regions of the body. For example, keeping the spinal region clear of pressure from the harness, by applying padding (900) on either side of the spine as in FIG. 9. And, in areas that must contact bony or sensitive regions, the pads may be added to reduce any discomfort. As will be appreciated the position and size of pads may be adjustable as well as the pads may be removable from the harness components. An optional feature, as depicted in FIGS. 3 and 4 for example, is a sliding strap 344 on the lower back of the harness. The strap allows the harness to be further adjusted across the back of the wearer and for articulation of the leg supports relative to the abdominal support when the wearer is walking or otherwise moving their legs.

Although not expressly illustrated, within the abdominal support and/or rear shoulder strap components, the harness may include a support structure such as stays, semi-flexible rods or the like. The support structure may be used to provide support for the wearer and/or to relieve a pressure point between the harness and the wearer (e.g., to displace pressure along the user's spine, parallel rods may be placed on either side and spaced apart from the spine).

Figure 7:
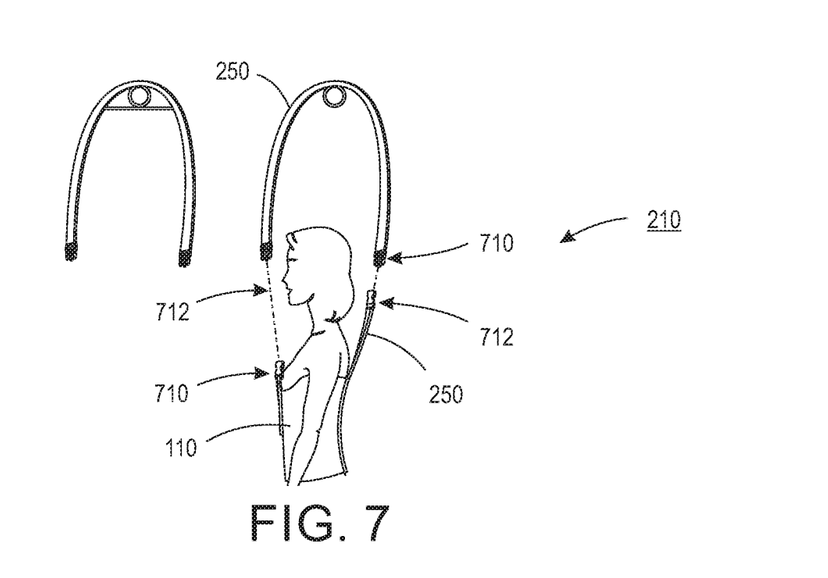
Figure 8:
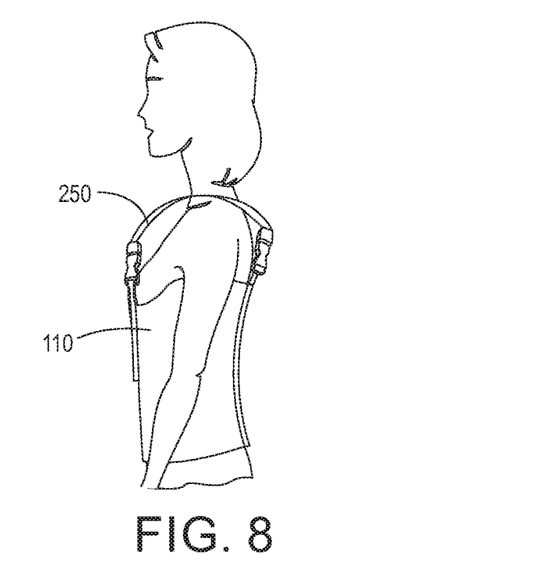

As will be appreciated, in one embodiment the straps 222 from spreader bar 220 may be connected to the harness (e.g., FIGS. 2 and 3) via D-rings 380 located on the front and back of the harness in association with the support straps. In an alternative embodiment, for example as depicted in FIGS. 7-8, the support straps 250 are each separable at a point between the front and back (e.g., upper-chest or shoulder region) so that they may be easily attached to mating straps, or more specifically mating buckle members (e.g., from a spreader bar overhead) and more easily donned. Thus, as represented by FIG. 8, the straps 250 initially remain buckled when the harness is being adjusted and fit to a wearer, thus ensuring proper position. However, once the harness is fit to the wearer, the shoulder straps may be unbuckled from one another and the open ends of the buckles that were separated are attached to mating buckle members on the ends of support straps 222. As illustrated in FIG. 7, a combination of male 710 and female 712 buckle pieces may assure that proper configuration and attachment between the spreader bar and harness. In summary, the pair of shoulder straps are both separable along their longitudinal length at a position near the shoulders such that the straps may be separated once the harness is positioned and the free ends of the straps are then connected to mating attachment devices on straps hanging from the spreader bar.

Figure 5:
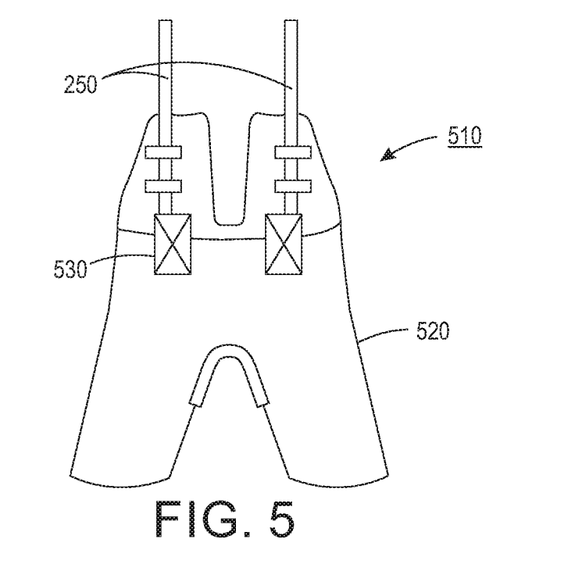

In the alternative leg support illustrated in FIG. 5, the leg support feature or component may also be accomplished using a shorts-like garment or wrapping component 510 that generally encompasses the wearer's lower torso and upper legs. Referring to FIG. 5, the shorts may be seamed or split along the sides 520 or other locations, and then once the person is seated on at least one portion of the shorts-like support, the remaining portion(s) may be re-connected using overlapping flaps and Velcro® strips, straps, zippers, buckles, etc. As will be appreciated a wrapping or seamed configuration will avoid the necessity of pulling them over the person's feet, ankles, etc. Either in combination or in the alternative, the shorts-like leg support of FIG. 5 may be attached to an abdominal support of the harness 210 via the previously-disclosed buckles and straps or via a rigid ring or other member 530 that is itself attached to the support straps 250 to provide a means of supporting the person wearing the support. It is believed that such a configuration will further resist the harness slipping or sliding upward relative to the user's body as it supports the wearer's weight.

In yet a further alternative leg support embodiment, one or both leg supports may include features that are customized to the particular patient. For example, rather than a wrap-around support for a wearer's leg, the support may be in the form of a cup or pouch that would be suitable for use by an amputee. Or, in a further alternative, the support may be designed to attach to a prosthetic device so as to provide support while an amputee undergoes therapy with the device attached.

In the various embodiments illustrated, where releasable buckles or other fasteners are used, it is contemplated that such fasteners or buckles may generally require at least two-point contact for their release, thereby avoiding inadvertent or accidental release while supporting a person.

Another aspect of the disclosed embodiments, which is illustrated in FIG. 2, (region 298) includes an interior color of each harness or at least a component being color coded according to the size of the harness. Moreover, the interior color of each harness (e.g., light blue) component is a color contrasting with the exterior color (e.g., black) of the component such that the person or anyone observing the person can immediately identify any unfastened or mis-applied components when the interior color is clearly visible other than along the edge of the component (i.e., if correctly sized and applied, there should be little or no contrasting interior colors showing).

Another feature contemplated in accordance with the disclosed embodiments is the use of differing buckle sizes, shapes, colors, etc. to help guard against connecting the wrong buckle halves together when the harness is being fitted or donned by a wearer. At least at locations where there may be possibility of accidentally inter-connecting the wrong buckles (e.g., straps between the leg supports and the abdominal support), different size buckles would preclude them from being accidentally connected.

Figure 12:
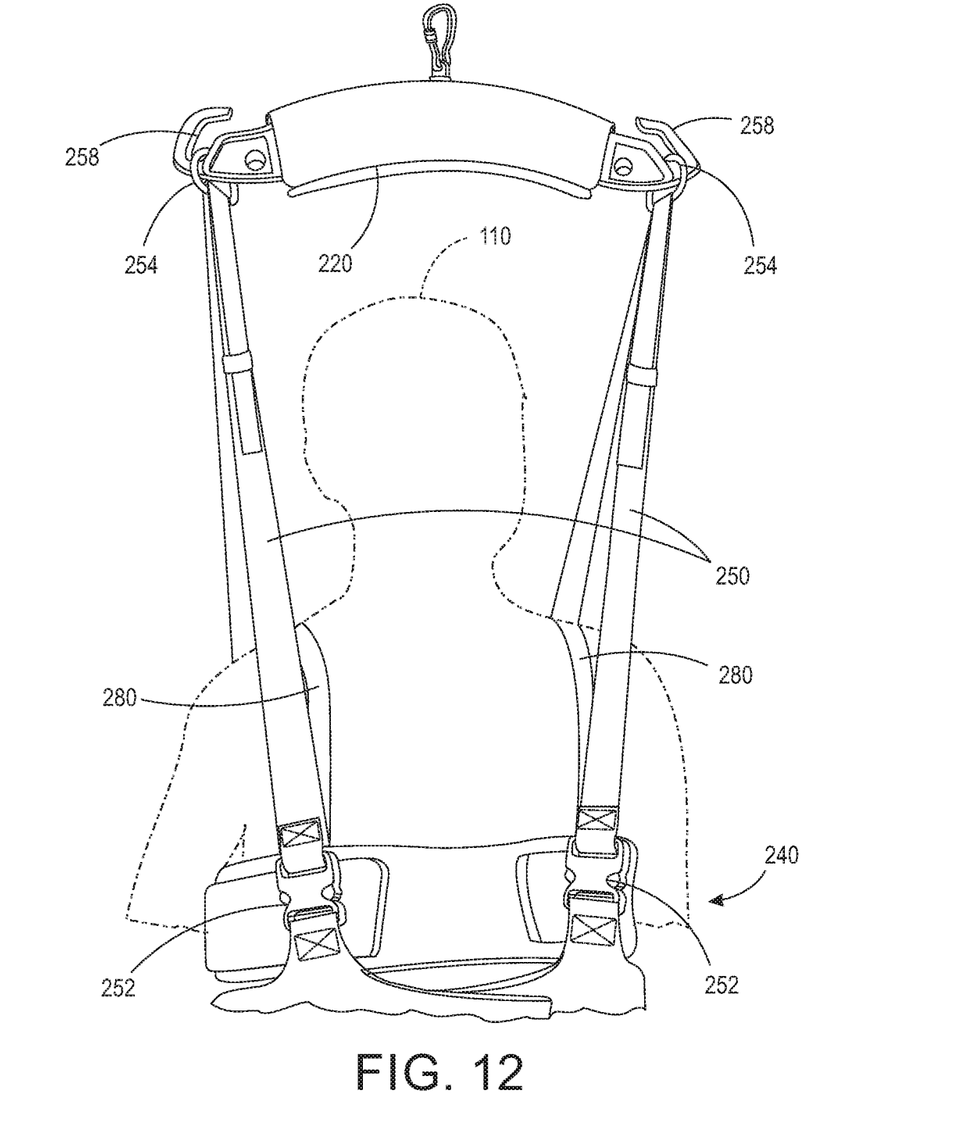
FIGS. 12-14 are, respectively, partial front, front perspective and rear perspective views of an alternative embodiment of the body harness.
Figure 13:
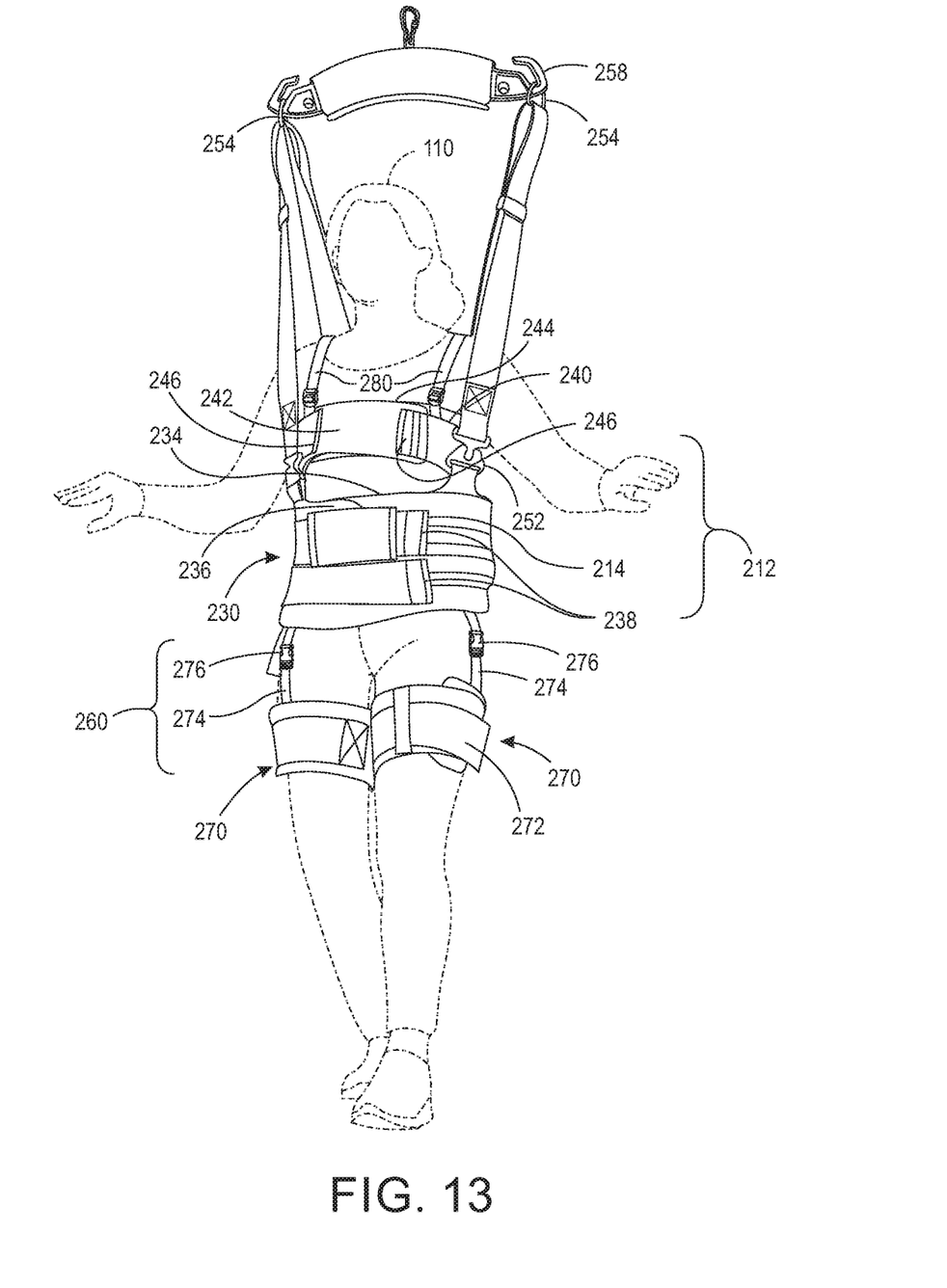
Figure 14:
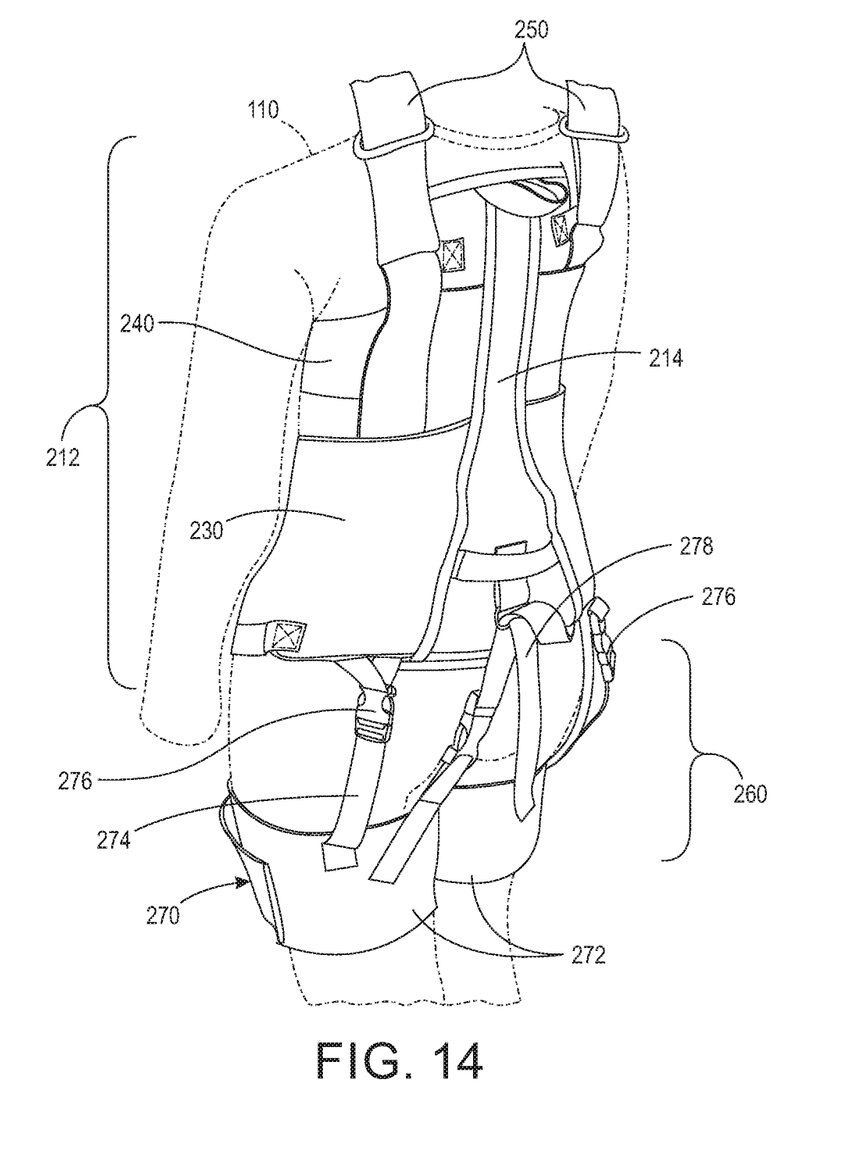

Reference is also made to FIGS. 12-14, wherein a further alternative embodiment of the disclosed body harness is depicted. In these figures the disclosed body harness includes various features that improve the comfort of the harness, as well as the support provided to a user. Body harness 210, comprises a torso support unit 212 including a padded posterior column 214. An adjustable abdominal support 230 is adapted to be placed around a torso of a user 110, at a location generally below the user's sternum. The abdominal support 230 includes an adjustable waistband 232 operatively connected to the posterior column, with padded waistband ends 234 and 236. One waistband end 234 may be placed in overlapping contact with an opposite waistband end 236 for securing using a hook-and-loop fastening system on the contacting surfaces. And, abdominal support 230 further includes at least one secondary waistband 238 encompassing at least part of the adjustable waistband for further cinching the adjustable waistband, by pulling the secondary waistband 238 and removably affixing it to an exposed outer surface of one of the waistband ends (234, 236). Torso support 212 also includes an adjustable chest band 240 operatively connected to said posterior column above the waistband, said chest band including chest band ends 242 and 244 where one chest band end may be placed in overlapping contact with an opposite chest band end for securing the two band ends to one another using a hook-and-loop fastening system as well. The chest band further includes at least one secondary chest band 246 encompassing at least part of the chest band for further cinching the chest band about the user.

Figure 6:
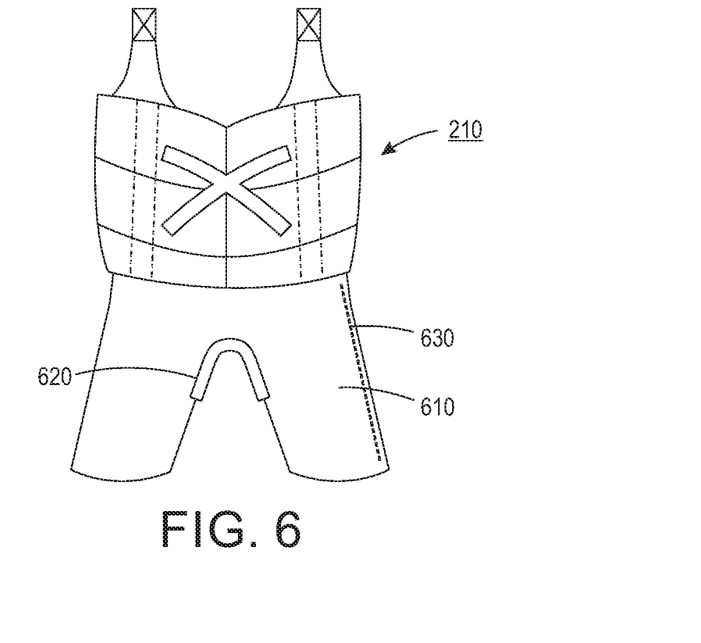

In addition to the torso support unit 212, the harness further includes at least one leg support 260 releasably suspended by adjustable straps from the torso support unit. As will be described in detail herein, the leg support may take the form of one or two leg cuffs 270, as well as the shorts 610 illustrated in FIG. 6. Shorts 610 may further include padding 620 at weight-bearing points, as well as a zipper 630 or similar fastening mechanism for releasably attaching the shorts to the user. Moreover, as illustrated, the shorts may be integrated with the torso component of the harness, or may be attached via straps such as with the leg cuffs described in the alternative embodiments.

The body harness also includes a pair of support straps 250 each operatively coupled at a first end to the torso support unit adjacent the top of the padded posterior column, and each releasably coupled at a second end to the torso support unit at a location on each of the respective waistband ends. As illustrated the support straps are releasably coupled via a buckle 252 adjacent the top of the waistband, and the user's weight is primarily supported by straps 250 via the cinched waistband—preferably located below the user's sternum. The straps 250 pass through a D-ring 254 that is held by the hooks 258 on the ends of spreader bar 220.

As further depicted in FIGS. 12 and 13, the body harness may include a pair of adjustable shoulder straps 280, the shoulder straps each extending from a first end attached to a location on each of the respective chest band ends, to a second end attached adjacent the top of the posterior column 214. The shoulder straps may be used to assist the user in donning the body harness, where they hold the chest band in position on the user 110.

As noted previously, the body harness in FIGS. 12-14 includes a posterior column 214. And, the posterior column may further include a postural support member. One or more of the posterior column and/or pads associated with the column may include supporting structures such as metal rods, molded foam padding layers (possibly including impact hardening foam to disperse load forces), straps and associated adjustments and connectors, along with breathable materials such as meshes and the like. And, at least a portion of the interior (user-contacting) surfaces of the posterior column 214, waistband 232 and a leg support(s) (e.g., leg cuffs 270) are each at least partially lined, and perhaps fully lined in the user-contact surfaces with a slip-resistant material. In one embodiment the slip-resistant material may include a rubberized or coated material providing resistance to slip relative to a user's clothing and/or skin.

Continuing with FIGS. 12-14, for example, body harness 210 has leg supports in the form of a pair of thigh pads or cuffs 270, each thigh pad 272 suitable for wrapping around one of a user's thighs, and being adjustably and releasably attached to the torso support unit via adjustable straps 274 and releasable buckles or clips 276. As shown in FIG. 14, the body harness may also include at least one assistive loop affixed to the torso support unit 212 adjacent the posterior column 214. The body harness may also include an assistive strap 278 releasably connected between said torso support unit 212 and each of the thigh pads 272.

As will be appreciated, several of the described harness components, particularly including the posterior column, waistband and chest band each may be entirely padded or may include padded portions where they are in contact with a user's body. Moreover, in the depicted alternative design, the various bands and cuffs each employ an overlapping hook-and-loop type fastening mechanism to facilitate the band or cuff being applied to a user while in a seated or standing position, and thereby avoiding the need for a user to have to put an arm, leg or head through any component of the body harness while donning the harness.

It should be understood that various changes and modifications to the embodiments described herein will be apparent to those skilled in the art. Such changes and modifications can be made without departing from the spirit and scope of the present disclosure and without diminishing its intended advantages.

It is therefore anticipated that all such changes and modifications be covered by the instant application.

What is claimed is:

1. A body harness, comprising:
    a torso support unit including:
        a padded posterior column,
        an adjustable abdominal support configured to be placed around a torso of a user at a location generally below a user's sternum, said adjustable abdominal support including a first waistband having a first padded waistband end and an opposite second padded waistband end, said first waistband being adjustable and operatively connected to said padded posterior column, where said first padded waistband end is placed in overlapping contact with said opposite second padded waistband end using a hook-and-loop fastening system for securing said first waistband around the torso of the user, said adjustable abdominal support further including at least one second waistband encompassing at least part of the first waistband for further cinching the first waistband, a first chest band, said first chest band being adjustable and operatively connected to said padded posterior column above the first waistband, said first chest band including a first chest band end and an opposite second chest band end, where said first chest band end is placed in overlapping contact with said opposite second chest band end using a hook-and-loop fastening system for securing said first chest band around a chest of the user, said first chest band further including at least one second chest band encompassing at least part of the first chest band for further cinching the first chest band, and a pair of adjustable shoulder straps, said pair of adjustable shoulder straps each having a first end and a second end, one of said pair of adjustable shoulder straps having the first end attached to said first chest band end and the second end attached adjacent a top of the padded posterior column, and the other of said pair of adjustable shoulder straps having the first end attached to said opposite second chest band end and the second end attached adjacent the top of the padded posterior column, at least one leg support, releasably suspended from said torso support unit; and a pair of support straps each operatively coupled at a first end to the torso support unit adjacent the top of the padded posterior column, one of said pair of support straps releasably coupled at a second end to the torso support unit at a location on said first padded waistband end, and the other of said pair of support straps releasably coupled at a second end to the torso support unit at a location on said opposite second padded waistband end.

2. The body harness according to claim 1, wherein the at least one leg support further includes a pair of thigh pads, each thigh pad of the pair of thigh pads wrapping around one of a user's thighs, and each thigh pad of the pair of thigh pads being adjustably and releasably attached to the torso support unit.

3. The body harness according to claim 2, further comprising at least one assistive strap releasably connected between said torso support unit and each thing pad of the pair of thigh pads.

4. The body harness according to claim 1 wherein said adjustable abdominal support includes a support structure selected from the group consisting of: stays, and semi-flexible rods.

5. The body harness according to claim 1 wherein said at least one leg support is separable and interchangeable to allow sizing of the at least one leg support separately from a balance of the body harness.

6. The body harness according to claim 1 wherein a spreader bar provides rings through which each of said pair of support straps are placed, such that support is provided to the user through at least one strap of said pair of support straps.

7. The body harness according to claim 1 wherein at least one of said adjustable abdominal support, said pair of support straps, said first chest band and said at least one leg support includes a buckle requiring at least two-point contact for release.

8. The body harness according to claim 1 wherein an interior color of each adjustable component of the body harness is color coded for a size of the body harness.

9. The body harness according to claim 1, wherein said padded posterior column includes a postural support member.

10. The body harness according to claim 1, wherein said first waistband and the at least one leg support are each at least partially lined with a slip-resistant material.

11. The body harness according to claim 1, wherein the first chest band further includes padding.

12. The body harness according to claim 1, wherein the body harness is applied to the user while the user remains in a seated position.

13. The body harness according to claim 1, further comprising at least one assistive loop affixed to said torso support unit adjacent the padded posterior column.

* * * * *